United States Patent [19]
Zahedi

[11] Patent Number: 5,893,891
[45] Date of Patent: *Apr. 13, 1999

[54] PROSTHESIS CONTROL SYSTEM

[75] Inventor: Mir Saeed Zahedi, Merrow, United Kingdom

[73] Assignee: Chas. A. Blatchford & Sons Limited, Hampshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/892,243

[22] Filed: Jul. 14, 1997

Related U.S. Application Data

[63] Continuation of application No. 08/250,469, May 27, 1994, abandoned.

[30] Foreign Application Priority Data

Jun. 11, 1993 [GB] United Kingdom ............ 9312131

[51] Int. Cl.$^6$ ................................ A61F 2/64; A61F 2/70
[52] U.S. Cl. ........................................ 623/24; 623/44
[58] Field of Search ........................ 623/24, 43, 44, 623/25; 414/5

[56] References Cited

U.S. PATENT DOCUMENTS

| | | |
|---|---|---|
| 4,246,661 | 1/1981 | Pinson . |
| 5,062,857 | 11/1991 | Berringer et al. ............ 623/25 |
| 5,443,524 | 8/1995 | Sawamura et al. ............ 623/24 |

FOREIGN PATENT DOCUMENTS

| | | |
|---|---|---|
| 0 380 060 | 8/1990 | European Pat. Off. . |
| 2 216 426 | 10/1989 | United Kingdom . |
| 2 252 503 | 8/1992 | United Kingdom . |
| 2 268 070 | 1/1994 | United Kingdom . |

OTHER PUBLICATIONS

Goldfarb et al, "Self–Contained, Microcomputer–Controlled, Above–Knee Prosthesis," *Proceedings, Seventh World Congress of ISPO*, Jun. 28, 1992, Chicago, U.S.A.

Flowers et al, "A Microcomputer–Controlled Knee Mechanism for Above Knee Prostheses", *Third CISM–IFToMM International Symposium on Theory & Practice of Robots and Manipulators*, 1978, Udine, Italy.

Peeraer et al, "A Computer–Controlled Knee Prosthesis", *Journal of Medical Engineering and Technology*, vol. 13, No. 1/2, Jan./Apr. 1989.

Koganezawa et al, "A Development of A/K Prosthesis Adaptable to Voluntary Walking Period", *Eighth International Symposium on External Control of Human Extremities*, 1984, Dubrovnik, Yugoslavia.

Arezina et al, "Development of a Control Programme for the Active Above–Knee Prosthesis", *Proceedings of Eighth International Symposium of ECHE*, 1984, Dubrovnik, Yugoslavia.

*Primary Examiner*—David H. Willse
*Attorney, Agent, or Firm*—Fish & Richardson P.C.

[57] ABSTRACT

An adaptive control system for an artificial limb has a piston and cylinder assembly for controlling knee joint flexion, an electronically driven motorised valve for varying the damping effect of the assembly, a proximity sensor for sensing knee flexion, and a processor circuit for mounting on the limb. The system also has a radio receiver connected to the processor circuit and an operator control unit for remote transmission of command signals to the receiver. In a teach mode, the system allows an operator to increment the valve opening by remote control to optimise operation of the limb, and to cause the processor circuit to record selected valve openings in conjunction with average step period values which are produced automatically by the system during use of the limb. Recording a new selected valve opening causes the processor circuit on the limb automatically to calculate a set of control data relating valve openings to walking speed ranges. This set of control data is used in a playback mode of the system for automatically adjusting the valve opening during normal use of the limb.

33 Claims, 6 Drawing Sheets

PROSTHESIS CONTROL SYSTEM

This is a continuation of application Ser. No. 08/250,469, filed May 27, 1994, now abandoned.

This invention relates to an adaptive prosthesis control system and a control method with specific relevance to the electrical control of knee flexion and/or extension in a lower limb prosthesis for an above-knee amputee.

British Patent Application No. GB 2216426A discloses a lower limb prosthesis having a pneumatic cylinder assembly interconnecting the thigh and shin components of the prosthesis to provide resistance to knee flexion and extension during the swing phase of the walking cycle. The cylinder includes a valve which is adjustable using a stepper motor to alter the degree of resistance according to signals received from a microcomputer control system which senses walking speed, so that resistance to movement of the shin component about the knee axis during the swing phase is varied as the walking speed varies. The control system is patient-adaptable in the sense that its operation is adapted to suit the individual amputee. This is achieved by operating the control system initially in a teaching mode and performing walking tests in which the system is calibrated at different walking speeds to achieve the best gait.

Experience has shown that operating the system in a teaching mode to achieve the best settings can be awkward and time consuming. It is an object of this invention to provide an improved control system which is more convenient in use.

According to one aspect of this invention, an adaptive prosthesis control system for an artificial limb comprises: a limb movement control device for mounting on the limb; a sensor for generating electrical sensor signals in response to movement of the limb; an electronic processing circuit electrically coupled to the sensor and the control device; a remote operator control unit for the transmission of command signals to the limb; and a receiver to form part of the limb and coupled to the processing circuit for receiving the command signals; wherein the processing circuit includes data generating means operable in a teach mode and a playback mode of the processing circuit automatically and repeatedly to generate measurement data values related to the speed of operation of the limb in response to the sensor signals, control device setting means operable in both modes to feed setting signals to the control device for adjusting a parameter of the control device, the setting means further being operable in the teach mode to feed the setting signals to the control device according to parameter values generated in the processing circuit in response to the command signals received by the processing circuit via the receiver from the remote control unit for adjusting the control device parameter under operator control during operation of the limb, means for processing the parameter values representing selected settings of the control device together with the associated said measurement data values to generate a set of control data representing a relationship between speed of limb operation and control device settings, and storage means for storing the set of control data, the setting means being further operable during the playback mode as the limb is operated to process the resulting said measurement data values in conjunction with the stored set of control data to generate the said setting signals for the control device, whereby the control device is automatically adjusted according to the speed of the limb operation.

The invention is particularly applicable to the control of an above-knee lower limb prosthesis, the control device being a knee flexion control device, and the control device parameter being the resistance of the device to movement at the knee joint. In this way it is possible for a prosthesis to calibrate the control system by a series of relatively short walking tests using the remote operator control unit without the constraints imposed by having to stay close to the patient to make adjustments to the system. The determination of walking speed is automated and is continuously measured and updated by the processing circuit, thereby removing much of the effort associated with the prior system. The system allows considerable simplification of the calibration procedure bringing benefits in terms of a shorter procedure and the reduced possibility of patient fatigue.

In the preferred system in accordance with the invention, the processing circuit includes saving means responsive to a further command signal received via the receiver from the remote control unit to feed automatically to the storage means signals representative of the measurement data value and the parameter value associated with a selected instant in time for each of a plurality of different limb operation speeds. In addition, the data generating means may be arranged to store a step period value in a storage element repeatedly during the teach mode, the stored value in the storage element thereby being updated continuously to provide a signal representative of the step period existing immediately before a further command signal as mentioned above is received. The data generating means may also be continuously operable to generate the step period values as a running average of a plurality of step periods, and the processing circuit preferably include means for calculating automatically a series of step period boundary values based on optimum step period values determined during the teaching mode to define a series of speed ranges, this occurring automatically when the saving means responds to the further command signal from the operator unit.

In effect, the processing circuit in the limb provides on-line interactive processing in the teach mode in the sense that the operator control unit allows a command signal to be issued which initiates a test routine or test "window". The test routine or window is terminated by the saving means in response to the above-mentioned further command signal. Whenever the receiver is switched on, it is preferred that the processing circuit continuously provides data measurement values representative of the speed of limb operation and uses the stored control data set to set the control device using the setting means. When a command signal is issued to initiate the test routine or window, in particular a command signal which designates a particular walking speed, the processing circuit allows the operator to set the control device using the operator control unit, the set parameter value being stored in a special register so that when the further command signal is issued it is the parameter value in the special register that is saved. The test routine for that designated having been terminated, the control data set is recalculated and the processing circuit reverts to automatic setting of the control device using the recalculated control data set. The prosthesis may then continue in the teach mode by issuing another command signal, e.g. for different walking speed, again initiating a test routine or window, and so on until a satisfactory control data set is produced. This data set can then be stored in a more permanent form, thereby ending the teach mode. Thus the teach mode may be regarded as including a plurality of operator defined test windows for different walking speeds, between which the system automatically sets the control device.

The values of the flexion control device parameter obtained at different walking speeds at the selected instants referred to above may be used by the processing circuit to calculate automatically interpolated parameter settings to provide a complete set of parameter settings to correspond to the different step period ranges. Typically, the teach mode allows the operator to designate three walking speeds so that three average step period values are measured and stored together with three corresponding parameter values. In the preferred embodiment, the processing circuit is arranged to calculate from the stored data four boundary or threshold step period values defining boundaries between five speed ranges, which can be referred to as slow, medium slow, normal, medium fast, and fast. These boundary values are stored in a non-volatile memory along with the three optimum parameter values determined during the walking tests and two automatically calculated intermediate parameter values to yield a set of five parameter settings for use during the playback mode according to which of the five step period ranges the step period corresponds at any given time during use of the prosthesis.

It is preferred that the communication link between the operator unit and the receiver is a one-way radio frequency link. The control unit may simply possess keys for designating walking speeds (e.g. slow, normal, fast), one or more controls for increasing and decreasing the flexion control device parameter value, and a control for saving optimum parameter values determined during the walking tests in conjunction with concurrently measured step period values.

The preferred knee flexion control device is a pneumatic piston and cylinder assembly interconnecting a thigh component of the prosthesis with a shin component so as to resist flexion and/or extension to varying degrees according to the degree of opening of a stepper motor adjustable valve in the piston. The preferred flexion control device parameter is thus resistance to flexion or extension, which may be expressed as the orifice area of a passage in communication with one or both cylinder spaces defined within the cylinder by the piston and the cylinder walls. The sensor may be a magnetic proximity sensor associated with the piston and cylinder assembly, comprising a permanent magnet mounted on or associated with the piston and a magnetically sensitive transducer mounted on or associated with the cylinder (or vice versa) to produce a pulsed electrical signal, one pulse being generated for each step taken. From this pulsed signal it is possible to determine the step period. It is to be understood that, while the step period is used in the description of the invention in this specification as a measure of the speed of walking, it is also possible to use signals directly or indirectly representing the step rate or speed.

The preferred embodiment includes means for counting the number of steps to generate a record of limb use.

According to another aspect of the invention, there is provided a method of controlling an artificial limb in which, during a teach phase, movement of the limb is automatically and repeatedly monitored by electronic means forming part of the limb with a series of measurement data values related to the speed of operation of the limb being generated in the electronic means, a remote control unit is operated in conjunction with a receiver forming part of the limb during operation of the limb to transmit command signals to the limb which are processed by the electronic means to generate setting signals for adjusting a limb movement control device of the limb with the object of improving limb operation, data generated in the electronic means and representing selected settings of the control device are processed in the electronic means together with the associated said measurement data values to generate a set of control data representing a relationship between speed of limb operation and control device settings, and the set of control data is then stored in the electronic means, and in which method, during a playback phase, the movement of the limb is automatically and repeatedly monitored by the electronic means to generate a series of measurement data values related to the speed of operation of the limb which are the processed by the electronic means in conjunction with the stored set of control data to generate appropriate control device setting signals for automatically adjusting the control device according to the speed of limb operation. Preferred features of the method of the invention are set out in the dependent claims.

The invention also includes a lower limb prosthesis including the knee flexion control device, processing circuit and receiver of the control system referred to above, the control device being secured to a thigh component and a shin component of the prosthesis. The combination of the prosthesis and the operator remote control unit constitute a limb system which allows a prosthesis to calibrate the prosthesis in a particularly effective and efficient way.

The invention will now be described by way of example with reference to the drawings in which.

Figure 1:
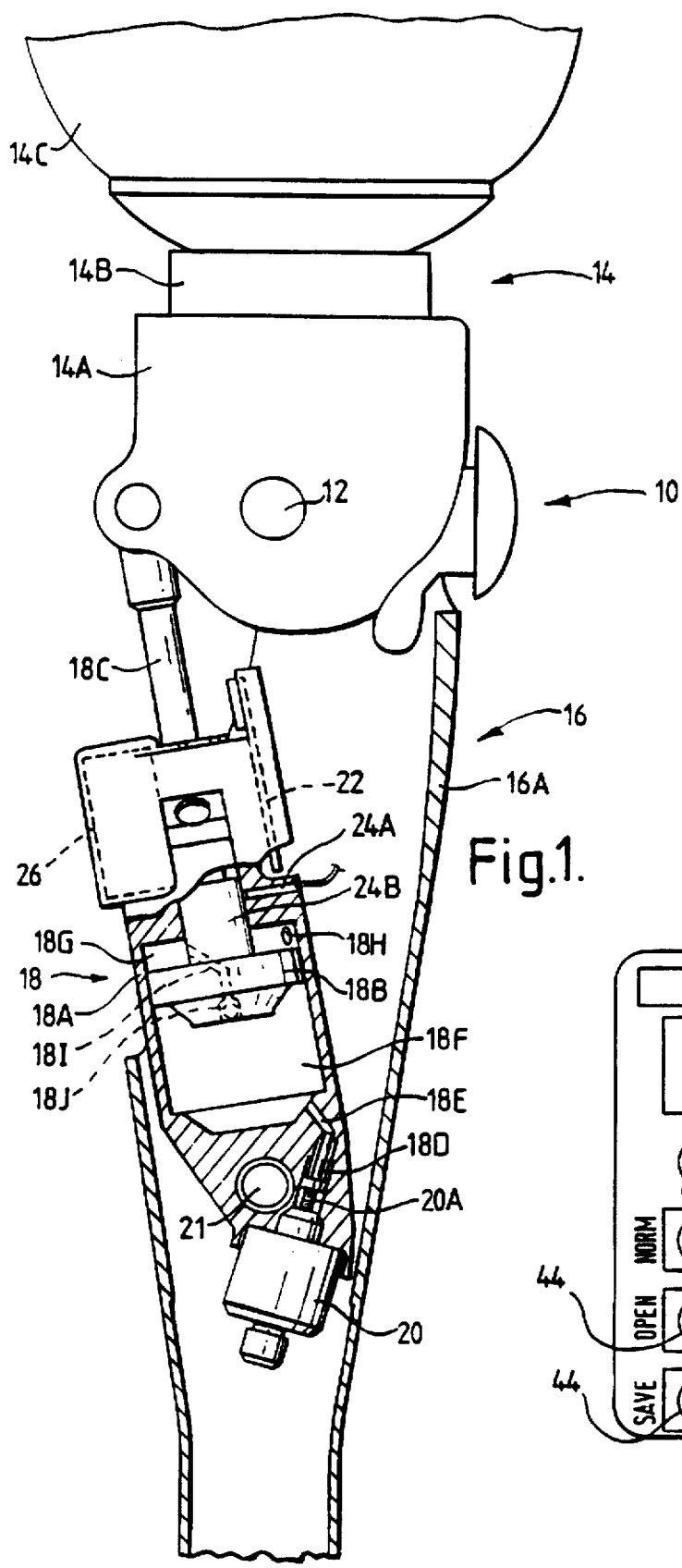
FIG. 1 is a partly sectioned side elevation of part of a lower limb prosthesis incorporating a flexion control device and electronic control elements.

A lower limb prosthesis incorporating part of a control system in accordance with the invention is shown in FIG. 1. The prosthesis has a knee joint 10 with a knee pivot 12 connecting a thigh component 14 to a shin component 16. The thigh component comprises a knee chassis 14A, an alignment device 14B, and a stump socket 14C. The shin component 16 has a conventional carbon fibre reinforced plastics shin cradle 16A which houses a piston and cylinder assembly 18 acting as a flexion control device. The assembly 18 comprises a cylinder 18A which is pivotally coupled to the posterior part of the shin cradle 16A and a piston 18B having a piston rod 18C which is pivotally coupled to the knee chassis 14A. The piston and cylinder assembly 18 is a pneumatic device, the resistance to flexion of the knee joint being controlled by a needle valve 18D which is adjustable by an electrical stepper motor 20 and an associated screw-threaded shaft 20A connected to the needle member of the needle valve. The needle valve 18D lies in a passage 18E in the body of the cylinder 18A, the passage 18E interconnecting the cylinder interior spaces 18F, 18G on opposite sides of the piston 18C, the passage emerging at a port 18H in the wall of the cylinder. Operation of the motor 20 causes the shaft 20A to move axially so that the needle member moves into or out of a passageway forming part of passage 18E.

The passage 18E constitutes a first bypass passage interconnecting the cylinder spaces on opposite sides of the piston 18C. A second bypass passage 18I incorporating a valve such as a one-way valve 18J is formed in the piston 18C so that the needle valve 18D is effective only on one stroke of the piston, in this case the stroke corresponding to increasing flexion of the knee joint 10. The one-way valve 18J may be arranged so as not to close-off the second bypass passage 18I completely on the increasing flexion stroke, but rather merely to reduce the orifice area through the piston 18C. Such an arrangement has the effect of the needle valve 18D determining the resistance to motion of the piston 18C in both directions, i.e. for increasing and decreasing flexion, but with the effect of variations in the orifice area of the needle valve 18D being greater in one direction than the other, depending on the direction of operation of the valve 18J.

It is also possible to include a one way valve in the passage communicating with port 18H. The stepper motor 20 and its threaded shaft 20A are mounted in the body of the cylinder 18, preferably adjacent the pivotal coupling 21 of the cylinder 18 to the shin 16.

The stepper motor is driven by the combination of a microcomputer and receiver which together form assembly 22. The microcomputer determines knee flexion and extension movements by means of a magnetic proximity sensor comprising a first part, preferably a transducer 24A, mounted in or associated with the cylinder 18A (a second part, preferably) a permanent magnet 24B mounted on or associated with the piston 18B. The electronic circuitry 22 and the stepper motor 20 are powered by batteries, one of which is shown in FIG. 1 and indicated by the reference 26. The receiver has a receiving antenna formed as a conductor track on the printed circuit board bearing components of the microcomputer and receiver.

Figure 2:
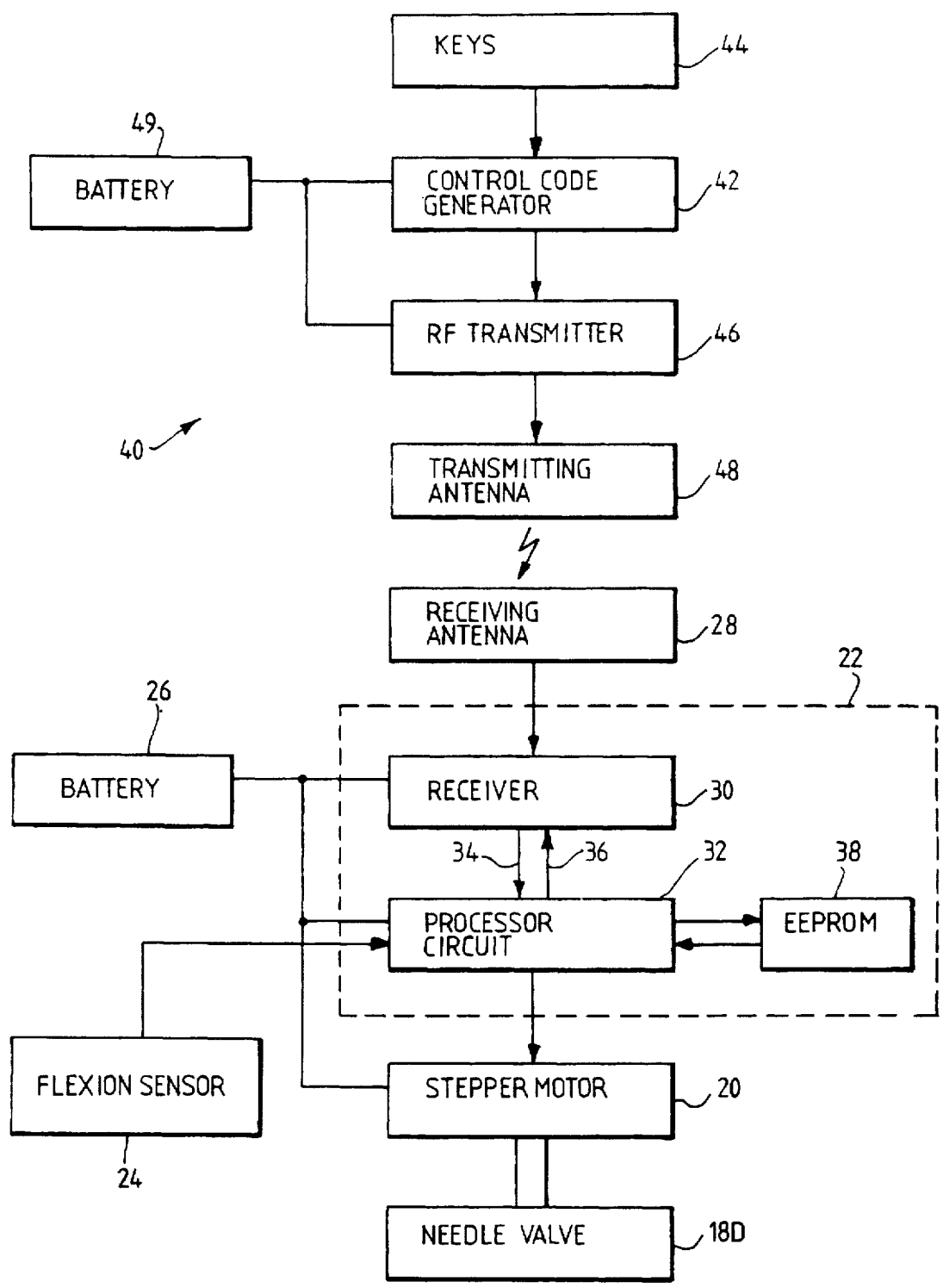
FIG. 2 is a block diagram of a prosthesis control system in accordance with the invention.

The electronic circuitry 22 is shown in more detail in FIG. 2. More particularly, the circuitry comprises the receiver 30 coupled to an antenna 28 and a processor circuit 32 which receives demodulated signals via input 34 and controls the receiver via output 36. A non-volatile memory in the form of an EEPROM 38 stores walking speed and valve setting data 38 produced by the processor circuit 32, and writes such data to the processor circuit 32 when required.

The processor circuit 32 includes an output driver for driving the stepper motor 20 which in turn moves the needle valve 18D, and it has an input for receiving pulses from the flexion sensor 24 comprising transducer 24A and magnet 24B (See FIG. 1).

Figure 3:
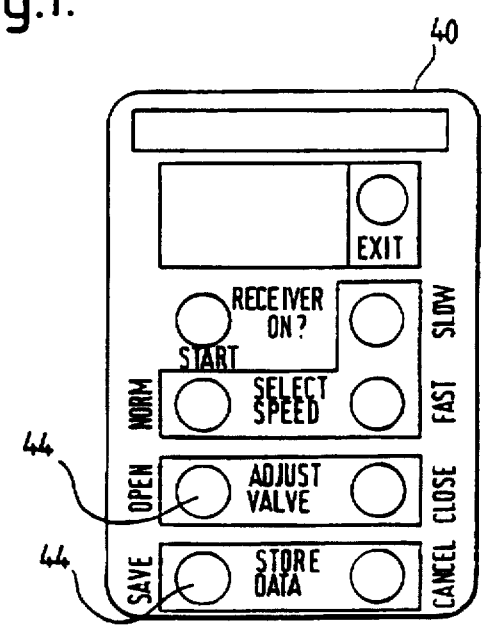
FIG. 3 is a plan view of an operator control unit.

The receiver 30 preferably receives radio frequency (RF) signals via the receiving antenna 28 from an operator control unit 40 shown in block diagram form in FIG. 2 and in plan view in FIG. 3. The control unit 40 has a control code generator 42 responsive to operation of keys 44 on the face of the control unit 40. The control codes generated by the generator 42 are modulated and transmitted by an RF transmitter 46 which feeds RF output signals to a transmitting antenna 48 within the control unit 40 for transmission to the receiving antenna 28 on the limb. A battery 49 housed within the control unit 40 powers both control code generator 42 and the transmitter 46.

Referring to FIG. 3 the keys of the control unit 40 are divided into four groups. The first group comprises START and EXIT keys which are used by the prosthesis to start and exit a teach mode of the control system for programming optimum valve settings for different walking speeds. The receiver 30 on the limb has a beeper (not shown) which sounds whenever one of the keys 44 is pressed and a corresponding signal is received, allowing the prosthesis to check the receiver is on and within range.

A second group of keys is for designating particular walking speeds. These SELECT SPEED keys comprise a SLOW key, a FAST key, and a NORM (normal) key. Thus, when the prosthesis wants to carry out a walking test at a normal speed, he presses the NORM key and the system then performs a teach sequence for that particular speed. The SLOW and FAST keys are used similarly for designating walking tests as slow and fast tests respectively.

During the walking tests, the prosthesis adjusts the swing phase resistance produced by the flexion control device using a group of ADJUST VALVE keys comprising an OPEN key and a CLOSE key for respectively decreasing swing resistance and increasing swing resistance. A SAVE key and a CANCEL key are used for saving optimum resistance (i.e. orifice size or area) settings and for erasing unwanted settings. In this manner the prosthesis can improve and, indeed, optimise the functioning of the control device at different limb operation speeds. In effect, the system is calibrated so as to be able to adjust the control device automatically to suit the individual wearer.

The receiver 30 or processor circuit 32 may include means (not shown in the drawings) for giving a visual or audible signal when the receiver is switched on and/or when particular keys are pressed on the operator control unit.

Figure 4:
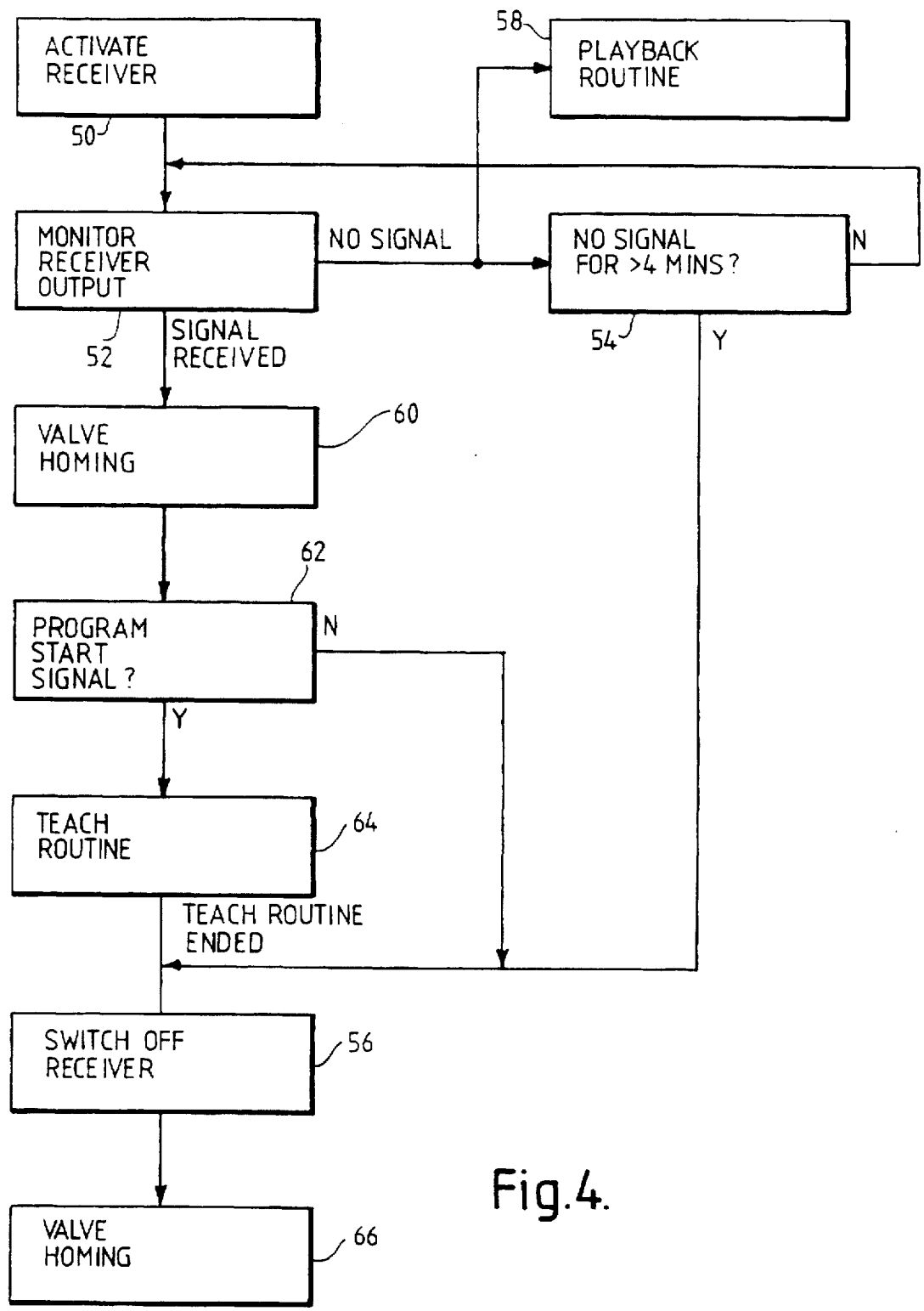
FIG. 4 is a flow chart illustrating start-up and shut-down phases of a program forming part of the control system.
Figure 5:
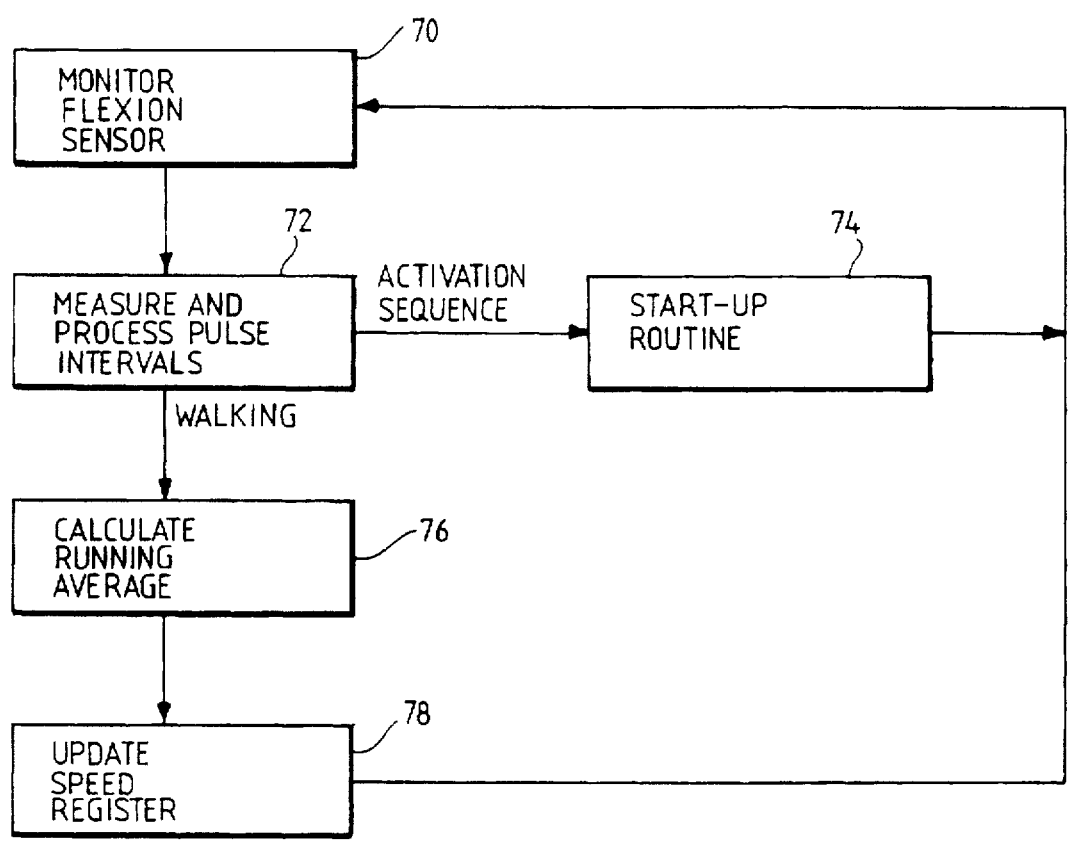
FIG. 5 is a teach mode speed measurement flow chart of the program.

Operation of the system will now be described with reference to FIGS. 4 to 7. Referring firstly to FIG. 4, which shows start-up and shut-down phases of a program run by the microcomputer to cause the system to run in a teach mode, activation of the receiver 30, which remains off during a playback mode of the system to save battery power, is performed by flexing the prosthesis at the knee in a particular manner. Specifically, the patient flexes the limb fully, counts 10 seconds, then extends the limb within 10 seconds, and flexes it again. This produces a particular sequence of signals from the flexion sensor shown as 24A, 24B in FIG. 1 which are recognised by the processor circuit 32 as an activation code, and the receiver 30 is switched on via line 36 (FIG. 2) (step 50 in FIG. 4). Having activated the receiver 30, the software causes the processor circuit 32 to monitor the receiver output (step 52) for a signal from the operator control unit. In the absence of any signal for longer than a predetermined period (e.g. 4 minutes), the processor circuit 32 causes the receiver to be switched off again (steps 54 and 56). Absence of the signal from the operator control unit also causes the processor to operate the playback routine (step 58), which will be described below.

As soon as the signal from the operator control unit is detected, the processor circuit undergoes a valve homing procedure (step 60). This is a procedure to allow the step motor and needle valve of the knee flexion control device to be set with respect to a predetermined reference position. In fact, the stepper motor 20 (FIG. 1) is fed with 40 valve closing step signals to move the needle valve 18D to the fully closed position. This is designated the zero reference position by the processor circuitry. A default value of a valve setting for the inactive state or slowest walking speed, or a previously saved valve setting for the inactive state or the slowest walking speed stored in the EEPROM store 38 is then read into the processor circuit 32 which has a "sitting and standing" register set up for the setting. This causes the stepper motor to move from the zero reference position to the appropriate valve setting. The valve homing procedure of step 60 is now complete. It has the result that the valve is set initially to a datum setting for sitting, standing, or slow movements.

The processor circuit 32 now waits for the program START signal from the operator control unit (step 62). If this is received, the microprocessor circuit operates a teach routine (step 64) which will be described below. If not, the receiver is switched off. The end of the teach routine 64 also produces switching off of the receiver as represented by step 56, and the valve is homed again in step 66 (which is performed in the same manner as the valve homing step 60).

When the processor circuit 32 is operating in the teach mode, the processor circuit 32 continuously monitors movements of the limb in order to determine whether the limb is inactive, or, if the patient is walking or running, the speed of such walking or running. Thus, referring to FIG. 5, the flexion sensor is monitored in a monitoring step 70 insofar as pulses from the sensor are received in the microprocessor circuit 32. The spacing between the pulses is measured by a counter loop; (only two successive pulses are required to establish a measurement). These pulse intervals are processed to determine whether the movement of the limb is characteristic of the activation sequence described above. If so, the start-up routine 74 is activated (as described above with reference to FIG. 4). In all other cases, a running average of the step period is calculated (step 76). If the step period represented by the running average is greater than two seconds, a speed register set up by the processor circuit is reset (step 78) and the next step period is counted. If no movement is detected for a predetermined period such as four seconds, the circuit 32 is programmed to cause the stepper motor to drive the valve to a value stored in the EEPROM store for standing or sitting.

Averaging (step 76) may be performed by creating a predetermined number, e.g. six, of calculation registers and successively feeding them corresponding number (six) step period counts, each register commencing with a different step. Thus, a first calculation register receives the counts for, say, steps 1, 2, 3, 4, 5, and 6. The second calculation register stores the counts for steps 2, 3, 4, 5, 6, and 7, the third register receives the counts for steps 3, 4, 5, 6, 7, and 8, and so on, the contents of each register being added and divided to produce a respective average value so as to yield a running average by reading the successive calculated averages one after the other at the same rate as the registers are being filled. In practice, the average is calculated by counting how many steps are taken between resets of the registers, ignoring the first and second step periods, adding together the next four and dividing by four. Other methods of calculating a running average can be used. The running average is stored in a walking speed register which is being continuously updated with the new average values. In the teach mode, updating continues only so long as the values are representative of the patient walking.

It will be appreciated, that having determined the walking speed in the above described manner, and given stored data in the form of a look-up table of valve settings associated with particular walking speeds, it is possible during use of the prosthesis to set the valve dynamically according to walking speed. The manner in which this stored data is produced will now be described with reference to FIG. 6, which shows the teach routine performed by the processor circuit 32 which, it will be recalled, appears in the start-up and shut-down flow chart of FIG. 4 as step 64.

The teach routine involves the basic operations of a prosthesis using the operator control unit to designate certain walking speeds as "slow", "normal", or "fast", the patient being led through a series of walking tests at the different speeds while the opening of the needle valve of the flexion control device is adjusted by remote control using the operator control unit until a satisfactory gait is obtained in each case. The optimum valve settings so obtained are stored by "saving" corresponding signals, and performing calculations to derive intermediate values so that data is stored in "final" registers set up by the processor circuit 32 representing five speed ranges and five corresponding valve settings. When the receiver is switched off (step 56, FIG. 4) this data is read into the EEPROM (38 in FIG. 2).

Figure 6:
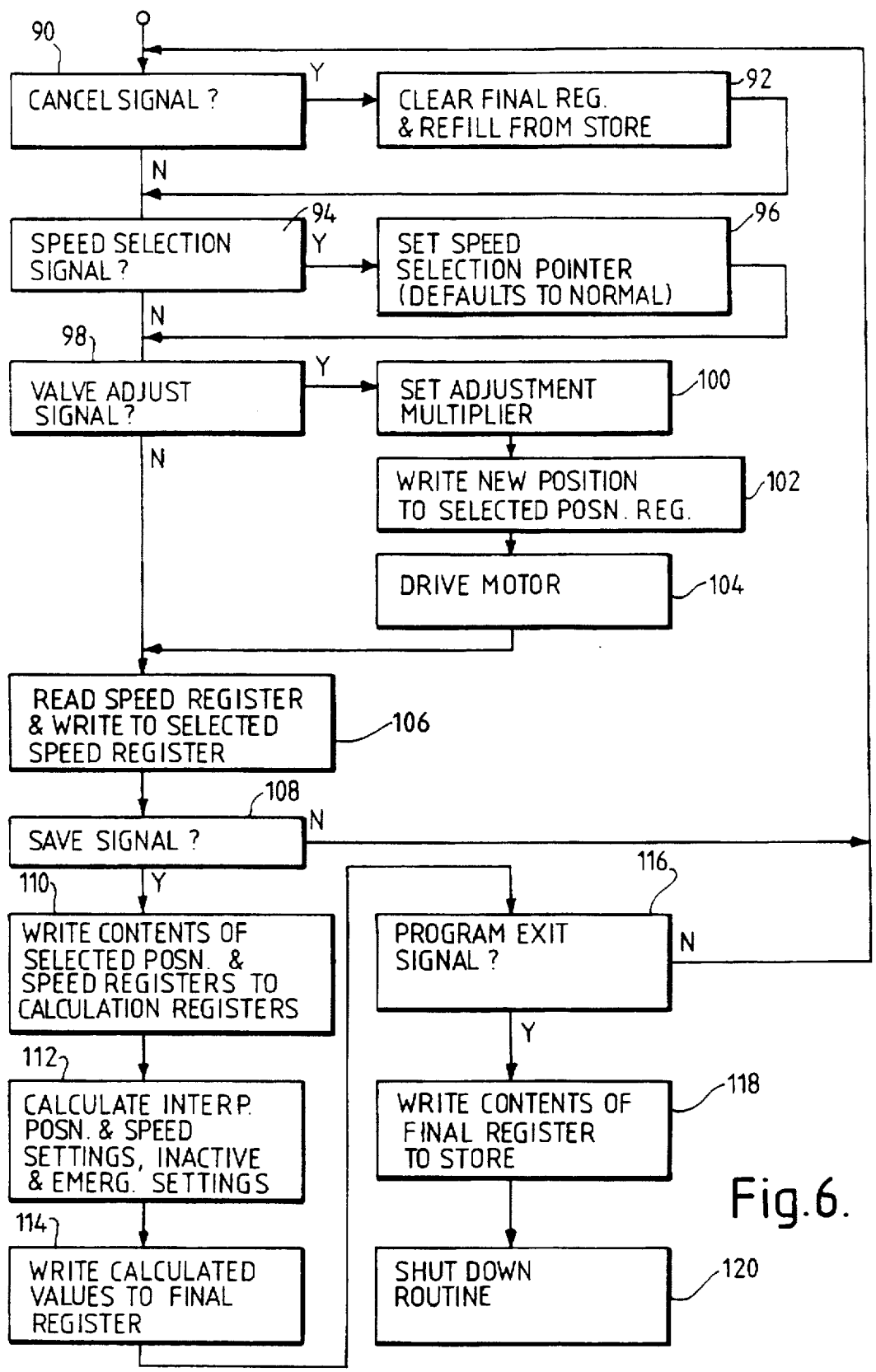
FIG. 6 is a teach routine flow chart of the program.

Now referring to FIG. 6, the teach mode begins with checking for receipt of a CANCEL signal from the operator control unit (step 90), receipt of such a signal causes the final registers to be cleared and refilled from the EEPROM store (step 92). Next, the program seeks a speed selection signal from the operator control unit. If this is received, a speed selection pointer is set either to slow, normal, or fast according to the signal received. In the absence of such a signal, the pointer defaults to normal (steps 94 and 96).

The processor circuit 32 thus now knows the selected speed to which the next part of the procedure relates. In step 98, the circuit looks for depression of either the OPEN (decrease resistance) or CLOSE (increase resistance) keys. Receipt of the signal corresponding to either causes the processor circuit to check the default settings of the standing and sitting register (referred to above in connection with the valve homing procedure) to determine the difference between the current valve position and the default setting so that the change in valve position resulting from one push of the OPEN key or CLOSE key is appropriately adjusted to the produce the same subjective effect substantially regardless of valve opening. Accordingly, if the current valve position is between, say, zero and 15 steps from the default position, a multiplier is set to cause the stepper motor to move at one step per key push. If, on the other hand, the current valve position is between 16 and 20 steps from the default position, the stepper motor is caused to move at two steps per key push, and so on with increasing steps for increasing difference from the default value. In effect, the multiplier is set to produce a logarithmic relationship between the valve movement and the valve opening with respect to the default position. These steps are representative in FIG. 6 by steps 98 and 100. A "selected position" register set up by the processor circuit 32 now receives the new valve setting, and the stepper motor is driven to cause the valve to move appropriately (steps 102 and 104). At this point the current value of the running average of the step period is read into a selected speed register representing the chosen designated speed (slow, normal, or fast) (step 106).

Next, the program checks for receipt of the SAVE signal from the operator control unit (step 108), and in the absence of such a signal returns to the beginning of the loop represented by steps 90 to 108. Initially, the teach routine allows the prosthesis to try a succession of different valve openings until the optimum setting is reached. At this point, the prosthesis presses the SAVE key to cause the program to proceed to step 110 in which the contents of the selected speed register, i.e. signals representing the last received running average step period and the last set valve position, are written to calculation registers. Of course, this step period and valve setting corresponds to just one of the selected speeds slow, normal, or fast. The calculation registers will already contain corresponding settings for the other two selected speeds, obtained either from previous walking tests or as default values.

Next, the processor circuit performs in step 112, calculation of boundary values for five speed ranges and five valve settings. This means that, in this preferred embodiment, the step periods measured for slow, normal, and fast walking tests are considered to represent the centre values of first, third, and fifth step period ranges, while step period values halfway between the slow and normal periods and normal and fast periods respectively are considered to represent the centre values of second and fourth step period ranges. The boundary values are calculated accordingly.

The three valve settings obtained from the calculation registers are considered to represent the optimum valve settings for walking speeds corresponding to step periods within the first, third, and fifth ranges respectively, while settings midway between the valve settings stored in the calculation register are considered as the optimum settings for speeds corresponding to step periods within the second and fourth step period ranges. Again, these intermediate valve settings are calculated in the calculation step 112. At the same time inactive and emergency settings of the valve are generated which correspond to the setting for the slowest speed range. This calculated step period range and valve setting data (five values for each plus inactive and emergency (low battery voltage) valve settings) are written to the final register each time a calculation is performed, i.e. after each SAVE command.

At this point, the prosthesis may have completed the walking tests, in which case he presses the program EXIT key which is sensed by the processor circuit in its checking step 116, causing the contents of the final register to be read to the EEPROM store (step 118) hence the program continues with the shut-down routine represented by steps 56 and 66 of FIG. 4 (step 120). If the prosthesis has not finished, no EXIT signal is received, and the teach routine is repeated from step 90 through to step 116 again.

It will be appreciated that the EEPROM now contains stored data representing five valve settings for five consecutive speed ranges which represent the optimum settings for the individual patient and which can be used during normal use of the prosthesis. It will be appreciated that a different number of speed ranges and corresponding valve settings can be used, the step period and the valve setting values being calculated appropriately. Indeed, discrete ranges may be dispensed with and the results of the walking tests may be used to define a continuous relationship between walking speed and valve opening, i.e. so that the valve opening can be altered in a stepless manner.

It is possible to incorporate a checking step in the teach routine whereby when the EXIT key is pressed, the program reads the relative magnitudes of the measured "slow", "normal" and "fast" step periods to check that the step periods are in the correct order of magnitude and, if necessary, re-allocates the "slow", "normal" and "fast" designations for the step period and corresponding valve setting values to put the step periods into the correct order. Incorrect ordering can happen when, for example, the walking tests are carried out at spaced apart times, and when the patient is tested alternately tired and not tired. If the valve settings are in an incorrect order of magnitude, the software is arranged such that one or both of the slow and fast settings is altered to be the same as the normal setting to avoid inconvenience for the patient until the tests are repeated.

Figure 7:
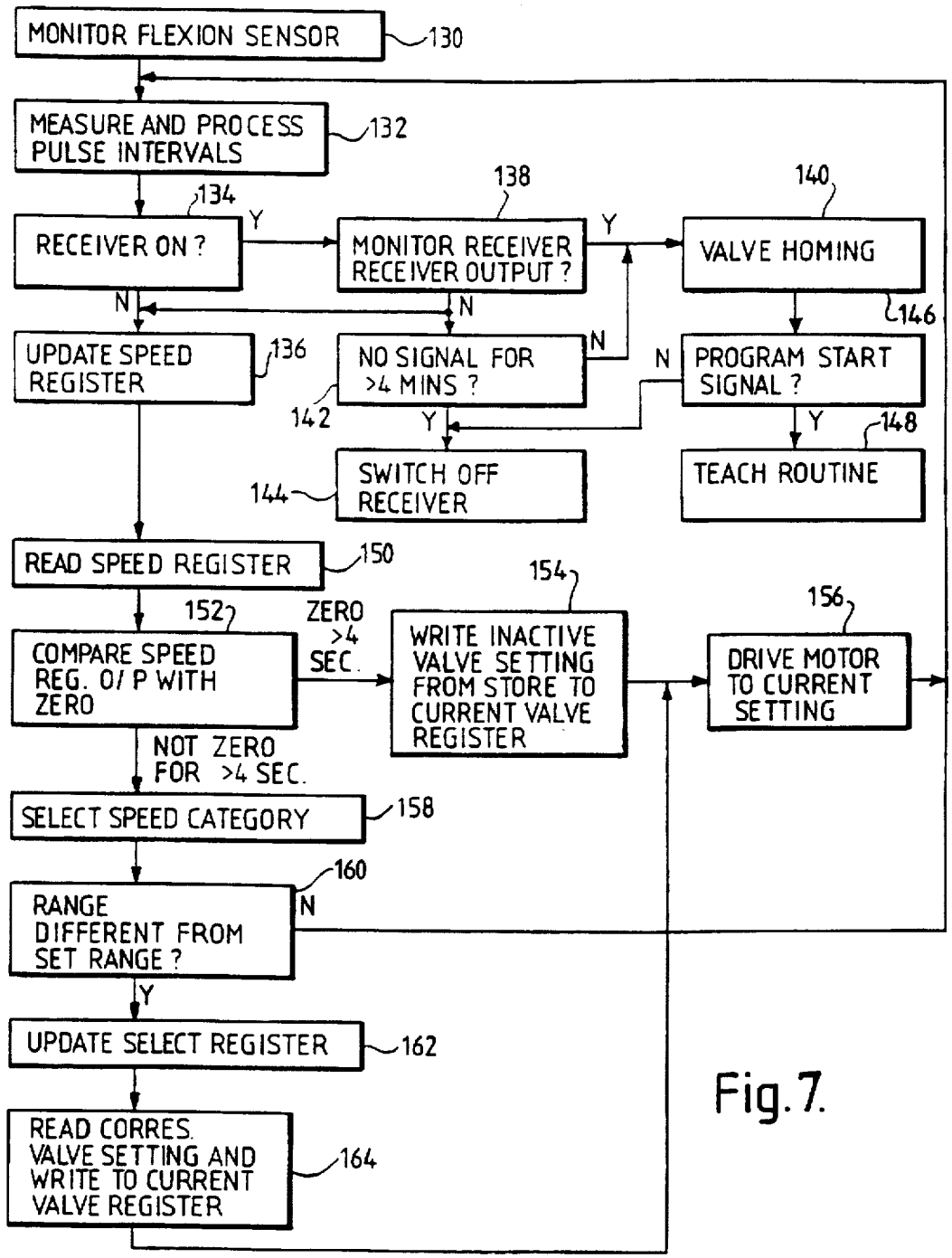
FIG. 7 is a playback routine flow chart of the program including playback mode speed measurement.

The playback routine will now be described with reference to FIG. 7. Referring to FIG. 7, the processor circuit first monitors the flexion sensor in step 130 and measures and processes the output in step 132 so that, after checking whether the receiver is activated in step 134 (see the description above for the activation procedure), the speed register can be updated with what can be referred to as the instantaneous value of the step period providing the receiver is off (step 136). In other words, rather than writing a calculated average step period value to the speed register as in the teach mode, the playback routine causes each measured step period to be written directly to the speed register so that changes in the patient's pattern of movement can be picked up immediately.

If the receiver is activated, however, checks are performed to determine whether to enter the teach mode. Accordingly the receiver output is monitored (step 138) for the presence of a signal from the operator control unit. If a signal is detected, the valve homing procedure described above with reference to FIG. 4 (step 140) is carried out. In the absence of such a receiver output signal, the speed register is updated with the so-called instantaneous step period value and then, while the playback routine is operating, the receiver output is monitored over a period of time, here four minutes, for the presence of an operator control unit signal, as shown in FIG. 7 as step 142. If a receiver output signal is detected during this period, again, the valve homing procedure is carried out. If not, the receiver is switched off (step 144) and the playback routine continues.

When a receiver output signal is detected, whether immediately or during the four minute period, and the valve homing procedure 140 has been carried out, the detection 146 of a program start signal from the operator control unit via the receiver causes entry 148 into the teach routine described above with reference to FIG. 6. If no program start signal is detected, the receiver is switched off and the playback routine is continued.

The next step in the playback routine, after updating of the speed register, is reading the speed register for the latest step period (step 150), followed by the comparison of the step period with zero (step 152). It should be understood that the contents of the speed register are zero so long as no flexion or extension is detected by the sensor 24A, 24B (FIG. 1) within a predetermined time interval. Thus, if the speed register output is zero for greater than four seconds, the prosthesis is considered to be inactive, in which case the inactive valve setting stored in the EEPROM store is read to a current valve register and the stepper motor is driven to the corresponding valve setting (steps 154, 156). The program then links back to step 132. If, however, movement is detected, and the speed register output is greater than zero for at least four seconds, the step period is compared with the boundary values of the step period ranges stored in the EEPROM (step 158) to determine whether the indicated range is different from the range already set in a select register (step 160). If no difference is detected, the program links back to the beginning of the playback routine. If a difference is detected, the select register is up-dated (step 162), the corresponding valve setting for the new range is read from the EEPROM store and written to the current valve register (step 164) and the motor is driven to the setting corresponding to the value in the current valve register (step 156). The program then returns back to the beginning of the playback routine.

The embodiment of the invention described above and shown in the drawings allows automatic control of knee movement to be programmed for most modes of use, from sitting and standing through slow walking, normal walking, and fast walking. It is possible, within the scope of the invention, to provide for programming for other modes of use such as running or other sporting activities. This can be done by extending the range of signals, e.g. step period values, which can be processed, and/or providing different patient-selectable modes. Thus, the control system may be operable in a walking mode in which the system is operated as described above, and in a special mode in which the same steps are performed in the teach and playback routines, except that different values are used in the registers. For initial programming, the prosthesis selects the walking mode, and performs the teach routine as described above. When the teach routine has been completed, and the program EXIT signal is given, the system operates in a playback mode as described above, using the values programmed for walking stored in walking registers.

In this alternative embodiment, the operator control unit has a further key or keys for selecting between the walking mode and the special mode. If, now, the prosthesis selects the special mode, then the teach routine can be performed with the patient performing special mode activities, and special mode data is stored in a new set of registers opened by the microprocessor.

The patient is provided with a hand held mode selection controller allowing the receiver to be switched on, the desired mode to be selected, and the receiver to be switched off. When special mode is selected, the playback routine uses the contents of the new registers.

Whether this alternative embodiment is used or the embodiment first described, the system has the advantage that since the operator control unit communicates via a wireless link the prosthesis can monitor the patient's performance from the most suitable position, and does not need to walk to the patient whenever a command signal is to be generated. Full automation of determination of walking speed and continuous measuring and updating of the walking speed by the processor circuit removes much of the effort involved in operating the prior art system for determining walking speed. The consequent significant simplification also reduces the extent of specialised training required of the prosthesis, and reduces the time necessary to reach optimum valve settings. As a result, it is possible in many cases for the patient to carry out the teaching procedure without intervention by the prosthesis, the patient benefitting by direct feedback without the need for interpretation by the prosthesis. In addition, the much reduced adjustment period significantly reduces the possibility of patient fatigue influencing the results.

The invention may be summarised, according to another aspect, as an adaptive prosthesis control system which comprises an electrically adjustable knee flexion control device for mounting in a lower limb prosthesis with a knee joint for controlling movement of the joint, a step sensor for generating a walking step signal indicative of the step period during walking, an electronic processing circuit associated with and electrically coupled to the flexion control device and the step sensor, a receiver electrically coupled to the processing circuit for receiving electromagnetically or acoustically radiated command signals, and an operator unit arranged to generate and radiate the command signals. The command signals include flexion control device adjustment signals which are transmitted by the operator unit under the control of an operator. The processing circuit includes storage means, speed indicating means operable automatically both in a teach mode and a playback mode to convert the walking step signal periodically into a step period value, and control device setting means responsive during the teach mode to the adjustment signals picked up by the receiver to cause alteration of a parameter of the flexion control device and to generate signals indicative of a value of the parameter. The processing means further comprises saving means responsive to a further command signal received via the receiver from the operator unit to feed automatically to the storage means signals representative of the step period value and the parameter value associated with a selected instant in time for each of a plurality of different walking speeds in order to produce a set of stored data representing required parameter settings for the different speeds. The processing means also include playback means operable in the playback mode to cause the flexion control device parameter to be adjusted at required times in accordance with the step period values derived from walking step signals sensed at those times by the step sensor and in accordance with the corresponding parameter settings of the stored data.

The system allows continuous processing and averaging of the walking speed or step period. In the teach mode the operator is able to alter the control device parameter by remote control, and to react in real time to each alteration by making further alterations. When a suitable setting for a particular speed of limb operation is achieved, the processing means can be remotely commanded to "save" that setting and automatically to calculate a new set of control data based on the new setting and previous settings for other walking speeds. The processing means is thus able to perform on-line calculation of control data for use in the playback mode. The processing means on the limb is automatically able to gather and process data. All operator commands are carried out by remote control in the preferred system.

What is claimed is:

1. An adaptive control system for an artificial limb, comprising:

a limb movement control device for mounting on the limb;

a sensor for generating electrical sensor signals in response to movement of the limb;

an electronic processing circuit electrically coupled to the sensor and the control device;

a remote operator control unit for the transmission of command signals to the limb; and a receiver to form part of the limb and coupled to the processing circuit for receiving the command signals, wherein the processing circuit includes;

data generating means operable in a teach mode and a playback mode of the processing circuit automatically and repeatedly to generate measurement data values related to the speed of operation of the limb in response to the sensor signals, control device setting means operable to feed setting signals in both modes to the control device for adjusting the control device so as to affect movement of the limb, the setting means further being operable in the teach mode to feed the setting signals to the control device according to parameter values generated in the processing circuit in response to the command signals received by the processing circuit via the receiver from the remote control unit to adjust the control device in real time under operator control during operation of the limb, means arranged to process the parameter values representing selected settings of the control device obtained during the teach mode together with the associated said measurement data values to generate automatically a set of control data representing a relationship between speed of limb operation and control device settings, and storage means for storing the set of control data, the setting means being further operable during the playback mode as the limb is operated to process the resulting said measurement data values in conjunction with the stored set of control data to generate the said setting signals for the control device, whereby the control device is automatically adjusted according to the speed of the limb operation.

2. A system according to claim 1, wherein in the control device is a knee flexion control device for mounting in an above-knee lower limb prosthesis and wherein the resistance to movement of the limb is affected by adjusting the control device.

3. A system according to claim 2, wherein the control device is a piston and cylinder assembly having a valve and an electric motor coupled to the valve for altering the degree of opening of the valve.

4. A system according to claim 2 or claim 3, wherein the sensor is arranged to produce pulsed sensor signals, one pulse being generated for each step taken.

5. A system according to claim 2, wherein the data generating means is operable continuously during the teach mode to generate measurement data values which are running averages of step periods as the limb is operated.

6. A system according to claim 2, wherein said system is incorporated in a lower limb prosthesis, the control device being secured to a thigh component and a shin component of the prosthesis.

7. A system according to claim 3, wherein the sensor has a first part mounted on the piston of the piston and cylinder assembly, and a second part mounted on the cylinder of the assembly.

8. A system according to claim 1, wherein the operator remote control unit includes a transmitter for transmitting the command signals to the receiver as electromagnetically radiated signals.

9. A system according to claim 1, wherein the processing circuit further includes saving means responsive to a further command signal received via the receiver from the remote control unit to feed automatically to the storage means signals representative of the measurement data value and the parameter value associated with a selected instant in time for each of a plurality of different limb operation speeds.

10. A system according to claim 9, wherein the processing circuit is operable in response to each operation of the saving means to calculate automatically a series of measurement data boundary values based on measurement data values selected during the teach mode to define a plurality of measurement data value ranges.

11. A system according to claim 10, wherein the processing circuit is operable automatically to calculate interpolated parameter values to provide a set of parameter values to correspond to the measurement data value ranges.

12. A system according to claim 1, wherein the remote control unit has control means for increasing and decreasing the control device parameters.

13. A system according to claim 1, wherein the processing circuit is arranged to be mounted on the limb together with the sensor and the receiver.

14. A system according to claim 1, wherein the processing circuit includes checking means for checking that the selected control device settings of said set of control data are correctly ordered in magnitude with respect to the corresponding stored measurement data values.

15. A system according to claim 1, wherein the means arranged to process the parameter values is responsive to a command signal generated in the remote control unit under operator control during the teach mode at the point when the adjustment of the control device has yielded a required control device setting, the command signal thereby causing the selection of the control device setting associated with a selected instant in time, and the parameter values processed include that representing said required control device setting.

16. A method of controlling an artificial limb in which, during a teach phase, movement of the limb is automatically and repeatedly monitored by electronic means forming part of the limb with a series of measurement data values related to the speed of operation of the limb being generated in the electronic means, a remote control unit is operated in conjunction with a receiver forming part of the limb during operation of the limb to transmit command signals to the limb which are processed by the electronic means to generate setting signals for adjusting a limb movement control device of the limb in real time with the object of improving limb operation, data generated in the electronic means and representing selected settings of the control device are processed in the electronic means together with the associated said measurement data values to generate a set of control data representing a relationship between speed of limb operation and control device settings, and the set of control data is then stored in the electronic means, and in which method, during a playback phase, the movement of the limb is automatically and repeatedly monitored by the electronic means to generate a series of measurement data values related to the speed of operation of the limb which are then processed by the electronic means in conjunction with the stored set of control data to generate appropriate control device setting signals for automatically adjusting the control device according to the speed of limb operation.

17. A method according to claim 16 for controlling knee movements of an above-knee lower limb prosthesis, wherein the selected settings of the control device correspond to different degrees of resistance to knee movement.

18. A method according to claim 17, wherein the control device is a piston and cylinder assembly and wherein operation of the control device comprises driving an electric motor to alter the degree of opening of a valve in the assembly.

19. A method according to claim 17, wherein the speed of operation of the limb is monitored using a sensor which produces a pulsed signal when the limb is operated, the electronic means measuring the pulse repetition rate.

20. A method according to claim 19, wherein the command signals are transmitted to the receiver as electromagnetic radiation.

21. A method according to claim 19, wherein the measurement data values are continuously generated by the electronic means as a series of running averages of the step period during both the teach phase and the playback phase as the limb is operated.

22. A method according to claim 16, including generating in the remote control unit a further command signal, and, in the electronic means, causing, in response to the further command signal, selection and storage of the measurement data value and the control device setting associated with the instant in time the further command signal is transmitted, whereby control device settings and measurement data values can be selected and saved for a plurality of different respective speeds of operation.

23. A method according to claim 22, wherein the processing of the selected control device settings and measurement data values to generate the control data set is performed in response to the said saving.

24. A method according to claim 22, wherein the processing of the selected control device settings and measurement data values comprises calculation of a series of measurement data boundary values based on the selected measurement data values to define a plurality of different consecutive measurement data value ranges, and wherein the processing of the control device settings comprises calculating interpolated settings to provide a set of control device setting values to correspond to the measurement data value ranges.

25. A method according to claim 16, wherein the command signals include control device incrementing signals for increasing or decreasing a parameter of the control device in steps.

26. A method according to claim 16, wherein the remote control unit is further operated to transmit a further command signal at the point when said adjustment has resulted in a required control device setting, the signal causing the electronic means to select the setting associated with a selected instant in time during limb operation, and said selected settings of the control device include said required control device setting.

27. A prosthesis control system for an artificial limb, comprising:

a limb movement controller arranged to control movement of the artificial limb;

a sensor arranged to generate a sensor signal having a characteristic representative of the speed of operation of the artificial limb;

a data storage device medium arranged to store a set of control data representing a relationship between settings of the controller and speeds of operation of the limb as represented by measurement values derived from the sensor signal;

an electronic processor arranged, in a playback mode, to receive the sensor signal and to feed to the controller first setting signals for controlling the movement of the limb, the setting signals representing the controller settings of the scored control data related to the measurement values obtained from the received sensor signal; and a command signal receiver arranged to receive operator command signals in a teach mode of the processor during operation of the limb;

wherein said processor is arranged, in the teach mode, to feed to the controller second setting signals in response to said command signals to adjust the controller so as to affect movement of the limb directly under operator control in real time during operation of the limb, to generate an updated set of control data representing a relationship between selected settings of the controller corresponding to said second setting signals and corresponding speeds of limb operation as represented by measurement values derived from the sensor signal, and to cause the updated set of control data to be stored in said data storage device medium for subsequent use in generating said first setting signals.

28. A system according to claim 27, further comprising a remote operator control unit for transmitting the command signals to the command signal receiver.

29. A system according to claim 27, wherein the electronic processor is further arranged, in the teach mode, to generate said measurement values as running averages of step periods during operation of the limb.

30. A system according to claim 27, wherein the remote operator control unit is arranged to transmit a data storing signal, the processor being arranged to respond to said data storing signal by causing the updated set of control data to be stored in said data storage device medium.

31. A system according to claim 27, wherein the processor is arranged to select under operator control a required adjusted control device setting associated with a selected instant in time during operating of the limb and wherein the updated set of control data represents a relationship involving the adjusted setting as well as other said selected settings of the controller.

32. A system according to claim 31, wherein the processor is arranged to generate the updated set of control data automatically at the time the adjusted controller setting is selected.

33. A system according to claim 32, wherein the processor is arranged to calculate the updated set of control data automatically each time a controller setting is readjusted.

* * * * *